(12) United States Patent
Fritzinger et al.

(10) Patent No.: US 9,763,680 B2
(45) Date of Patent: Sep. 19, 2017

(54) INTERCHANGEABLE DRILL BITS FOR DRILL ASSEMBLY

(71) Applicant: Biomet Manufacturing, LLC, Warsaw, IN (US)

(72) Inventors: Daniel Duane Fritzinger, Warsaw, IN (US); Brian Krehlik, Murfreesboro, TN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 488 days.

(21) Appl. No.: 14/484,750

(22) Filed: Sep. 12, 2014

(65) Prior Publication Data

US 2016/0074047 A1  Mar. 17, 2016

(51) Int. Cl.
*A61B 17/16* (2006.01)

(52) U.S. Cl.
CPC ........ *A61B 17/1684* (2013.01); *A61B 17/162* (2013.01); *A61B 17/1615* (2013.01); *A61B 17/1617* (2013.01); *A61B 17/1624* (2013.01); *A61B 17/1631* (2013.01); *A61B 17/1633* (2013.01); *A61B 17/1635* (2013.01); *A61B 17/1659* (2013.01)

(58) Field of Classification Search
CPC . A61B 17/1615; A61B 17/16; A61B 17/1635; A61B 17/1655; A61B 17/1617
See application file for complete search history.

(56) References Cited

U.S. PATENT DOCUMENTS

| | | | |
|---|---|---|---|
| 6,783,533 B2 * | 8/2004 | Green | A61B 17/1617 606/80 |
| 8,025,662 B2 * | 9/2011 | Knisely | A61B 17/16 408/227 |
| 8,795,279 B2 | 8/2014 | Winslow et al. | |
| 8,795,280 B2 | 8/2014 | Winslow et al. | |
| 2003/0097133 A1 | 5/2003 | Green et al. | |
| 2005/0149031 A1 | 7/2005 | Ciccone et al. | |
| 2006/0015110 A1 | 1/2006 | Pepper | |
| 2013/0090659 A1 | 4/2013 | Sasing et al. | |

FOREIGN PATENT DOCUMENTS

WO  WO-2016039889 A1  3/2016

OTHER PUBLICATIONS

"International Application Serial No. PCT/US2015/043391, International Search Report mailed Sep. 21, 2015", 4 pgs.
"International Application Serial No. PCT/US2015/043391, Written Opinion mailed Sep. 21, 2015", 6 pgs.

* cited by examiner

*Primary Examiner* — Andrew Yang
(74) *Attorney, Agent, or Firm* — Schwegman Lundberg & Woessner, P.A.

(57) ABSTRACT

A drill bit comprising a cutting portion having an edge for penetrating bone and a resilient tine configured to be inserted into a drill housing, the resilient tine including a tab having an abutment surface configured to establish a snap-fit connection with a drill gear within the drill housing, and wherein the drill bit is capable of being removed from the drill housing by disengaging the abutment surface from the drill gear.

10 Claims, 20 Drawing Sheets

INTERCHANGEABLE DRILL BITS FOR DRILL ASSEMBLY

TECHNICAL FIELD

The present invention generally relates to a drill bit for a drill assembly, and more particularly to an interchangeable drill bit for a peripheral peg drill assembly used during a glenoid replacement surgical procedure.

BACKGROUND OF THE INVENTION

The statements in this section merely provide background information related to the present disclosure and should not be construed as constituting prior art.

A natural shoulder joint may undergo degenerative changes due to a variety of etiologies. When these degenerative changes become so far advanced and irreversible, it may ultimately become necessary to replace a natural shoulder joint with a prosthetic shoulder joint. When implantation of a shoulder joint prosthesis becomes necessary, the natural head portion of the humerus can be resected and a cavity created in the intramedullary canal of the host humerus for accepting a humeral component. Moreover, the glenoid cavity positioned at the lateral edge of the scapula may also be resurfaced and shaped to accept the glenoid component. The humeral component includes a head portion used to replace the natural head of the humerus, while the glenoid component generally includes an articulating surface which is engaged by the head portion of the humeral component.

It is generally known in the art to provide a shoulder joint prosthesis having a glenoid component, as discussed above. Current glenoid replacement surgical techniques, however, suffer from some disadvantages, particularly as they require the surgeon to perform numerous bone preparation steps before the glenoid component can be surgically implanted. More particularly, since glenoid components are subject to various types of loading by the head portion of the humeral component, the glenoid component must offer a stable and secure articulating surface. To achieve this, some glenoid components provide peripheral pegs which are inserted and cemented into holes bored into the glenoid cavity. Some of the pegged glenoid components utilize up to five peripheral pegs in order to stabilize and secure the glenoid component to the scapula. Current glenoid replacement procedures require pre-drilled holes to be formed in the bone for each peripheral peg of the glenoid component. To achieve this, typically a guide is placed on the glenoid that provides a path for each peripheral peg hole to be drilled. After each hole is drilled, an anti-rotation peg is inserted into that respective hole of the guide to ensure the next drilled hole is properly aligned. By requiring multiple holes to be separately drilled into the bone, not only is the process time-consuming, but it also increases the possibility that a drilling misalignment will occur during the bone preparation process.

In addition to the process being complicated and time consuming, if the drill assembly is used several times, the drill bits often become dull and/or damaged. Moreover, if the drill bits are incapable of being replaced, the entire drill assembly must be discarded, which is not an economical solution.

What is needed then is a device that can be incorporated into a glenoid replacement surgical technique without suffering from the above-mentioned disadvantages. The present invention is intended to improve upon and resolve some of these known deficiencies of the art.

SUMMARY OF THE INVENTION

In accordance with one aspect of the present invention, a drill bit is provided and comprises a cutting portion having an edge for penetrating bone and a resilient tine configured to be inserted into a drill housing. The resilient tine includes a tab having an abutment surface configured to establish a snap-fit connection with a drill gear within the drill housing. The drill bit is capable of being removed from the drill housing by disengaging the abutment surface from the drill gear.

According to another aspect of the present invention, a drill bit is provided and comprises a cutting portion having an edge for penetrating bone; a shank portion configured to be inserted into a drill housing, the shank portion including a resilient tine that is movable from a first position to a second position; and a tab extending from the resilient tine, the tab including an abutment surface that is configured to snappingly engage a surface of a drill gear.

In accordance with still another aspect of the present invention, a drill assembly is provided and comprises a housing having a first side and a second side opposite the first side; a drill bit having a cutting edge for penetrating bone and a resilient tine configured to be inserted into the housing; and a driving mechanism having a drill gear configured to rotate the drill bit and penetrate the bone, the drill gear including a channel for receiving the resilient tine. The resilient tine includes a tab having an abutment surface configured to establish a snap-fit connection with a drill gear.

Still other objects and benefits of the invention will become apparent from the following written description along with the accompanying figures.

BRIEF DESCRIPTION OF THE DRAWINGS

The above-mentioned aspects of the present invention and the manner of obtaining them will become more apparent and the invention itself will be better understood by reference to the following description of the embodiments of the invention taken in conjunction with the accompanying drawings, wherein.

Figure 1:
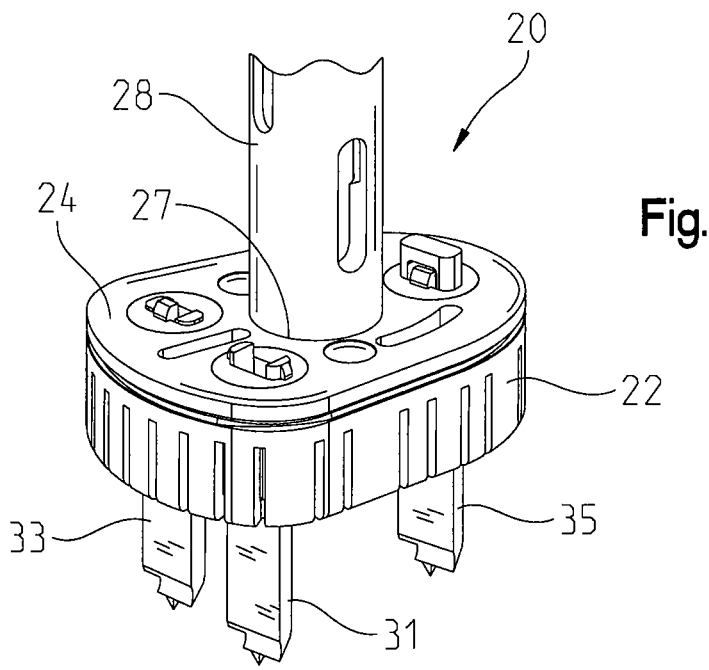
FIG. 1 represents a perspective view of a peripheral peg drill component according the present teachings.

Corresponding reference characters indicate corresponding parts throughout the several views. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Unless defined otherwise, all technical and scientific terms used herein have the same meaning as commonly understood by one of ordinary skill in the art to which this invention belongs. Although any method and materials similar or equivalent to those described herein can be used in the practice or testing of the present invention, the specific methods and materials are now described. Moreover, the techniques employed or contemplated herein are standard methodologies well known to one of ordinary skill in the art and the materials, methods and examples are illustrative only and not intended to be limiting.

Figure 2:
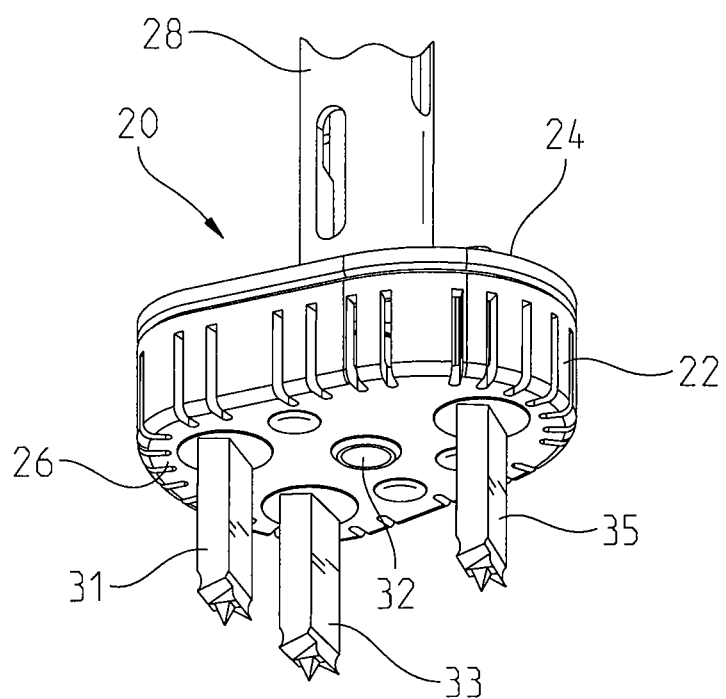
FIG. 2 represents a perspective bottom view of the peripheral peg drill component of FIG. 1.

Referring generally to FIGS. 1 and 2, perspective views of a peripheral peg drill component 20 according to the teachings of the present application are shown. The peripheral peg drill component 20 is defined by a housing 22 having a first side 24 and a second side 26. The first side 24 of the housing 22 includes a defined opening 27 that is configured to receive the drive shaft 28 of a drill, while the second side 26 has one or more drill bits 31, 33 and 35 extending therefrom and configured to create peripheral peg holes in a glenoid cavity upon actuation of the drilling device. In terms of the structural means by which the drive shaft 28 is connected to the housing 22 of the peripheral peg drill component 20, it should be understood and appreciated herein that any known connection means may be utilized without straying from the teachings and scope of the present application. For instance, in accordance with one specific illustrative embodiment, a conventional Hudson connection can be utilized. In accordance with yet other illustrative embodiments, the drive shaft can be releasably secured to the peripheral peg drill component 20 by a connection means including, but not limited to, a square-drive quick-connection, a conventional drill chuck mechanism, a set screw, a tool clamp, a rivet, a snap ring, a press-fit, or the like. As such, the present teachings are not intended to be limited herein.

As is particularly shown in FIG. 2, the second side 26 of the peripheral peg drill component 20 includes a substantially centralized and defined opening 32 that is configured to receive a guide or alignment pin 34 (see FIG. 5) that has been inserted into the glenoid cavity 36 as part of the glenoid preparation process.

Figure 3:
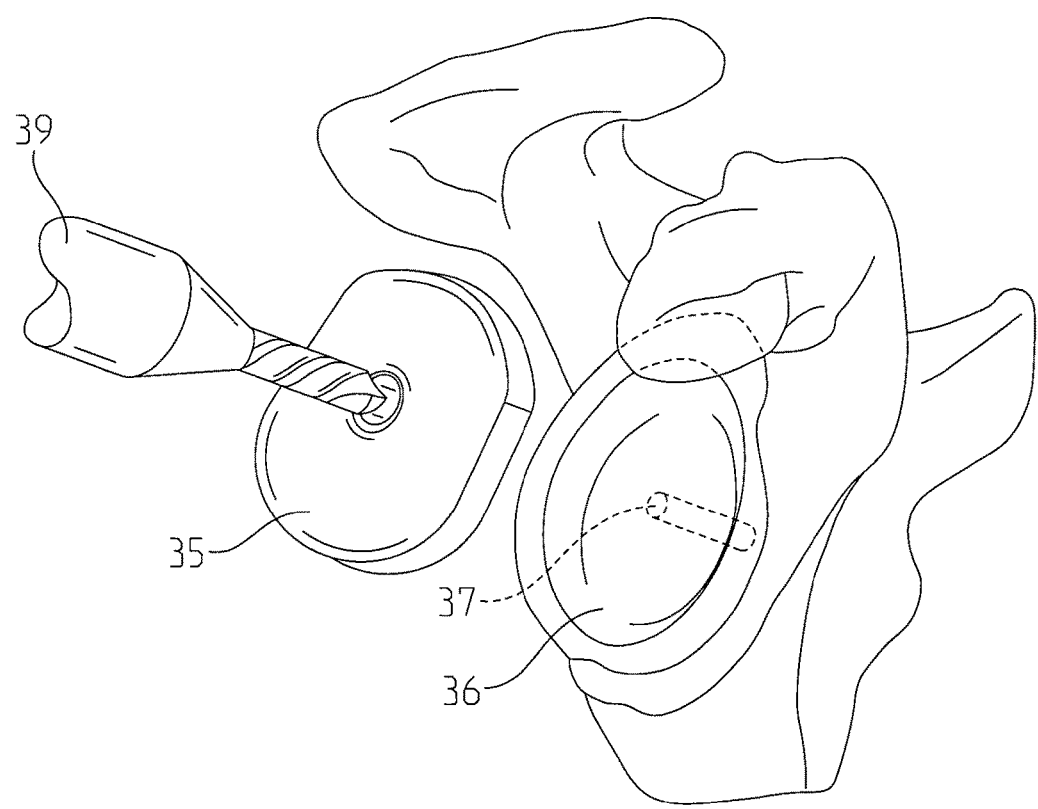
FIGS. 3-5 represent perspective views of a glenoid cavity being prepared prior to the implantation of a glenoid component according to the present teachings.
Figure 4:
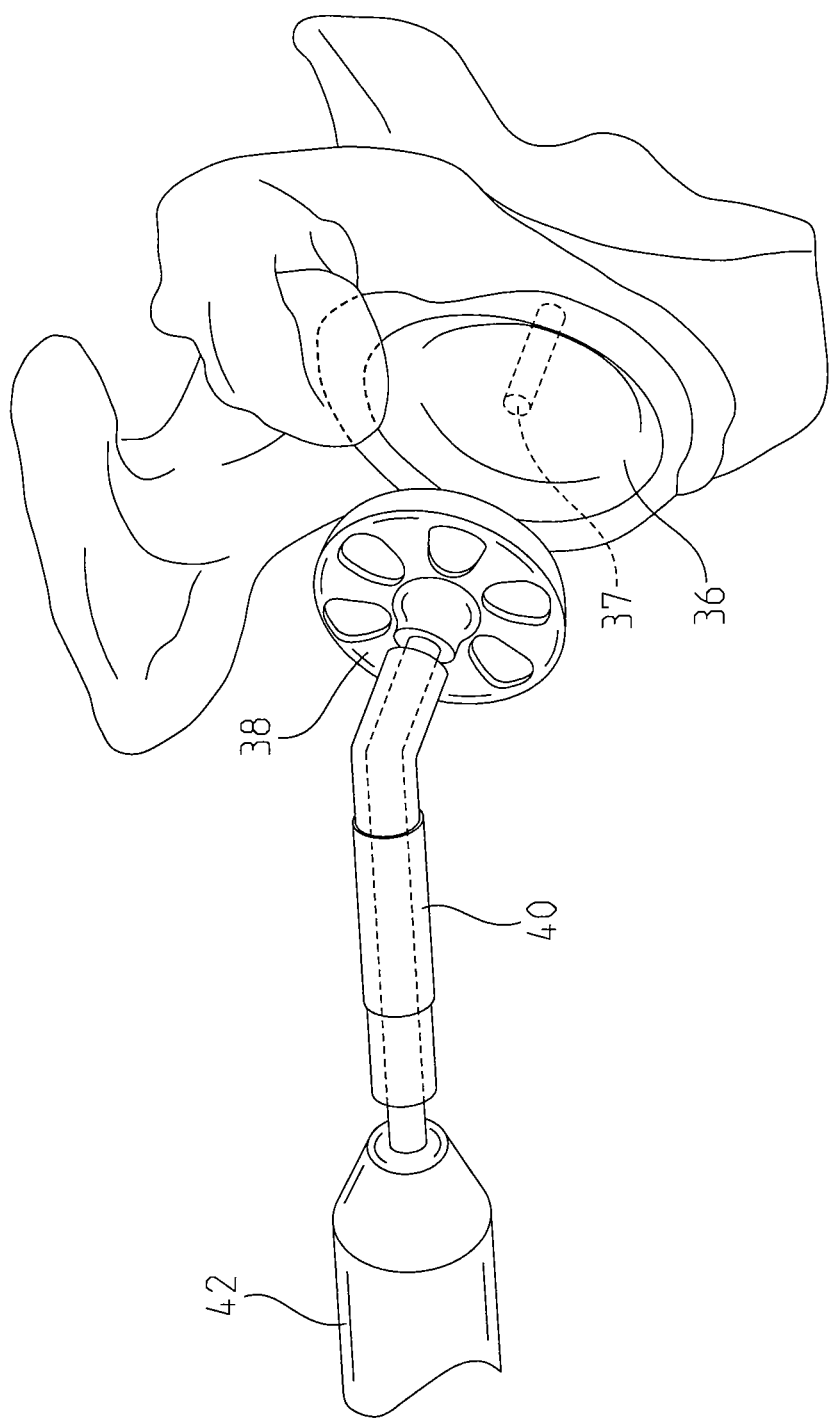
Figure 5:
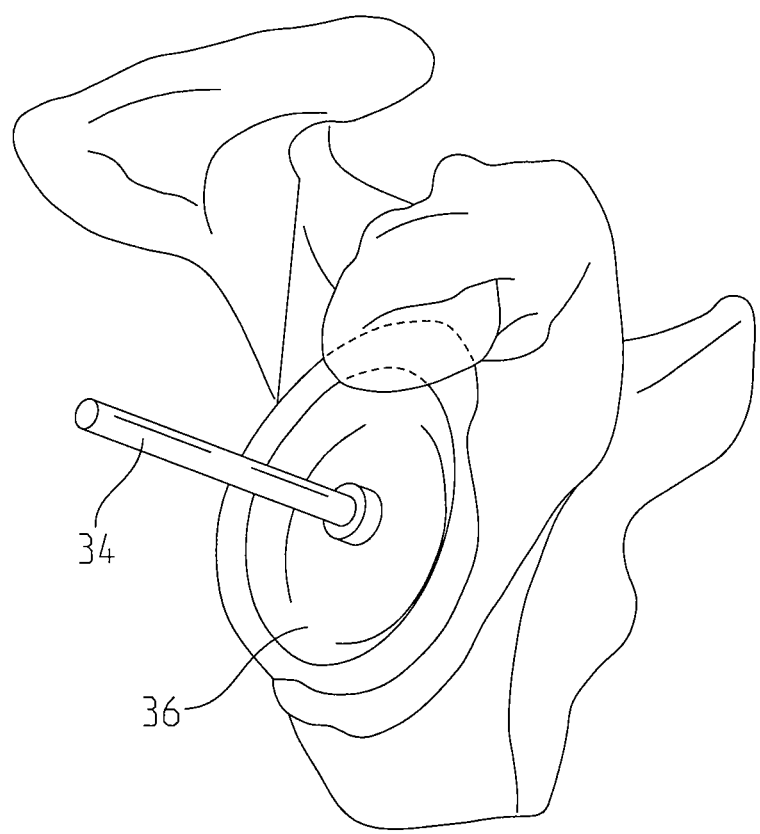

FIGS. 3-5 represent an illustration of an exemplary process for preparing a glenoid prior to implanting a glenoid component according to the teachings of the present application. As shown in FIG. 3, a drilling guide 35 can be used to create a central guide hole 37 into the surface of the glenoid cavity 36 using a drill 39. After the preparation of a central guide hole 37, as shown in FIG. 4, the glenoid cavity 36 is reamed using a glenoid surface rasp 38 and an angled reamer shaft 40 with driver 42. As those of skill in the art will understand and appreciate, the glenoid surface rasp 38 is configured to prepare a planar or curved glenoid surface to mate with the coupling side of the glenoid component to be implanted. To accomplish this, the glenoid surface rasp 38 may include a roughened spherical surface that substantially corresponds to the spherical shape of the medial surface of the glenoid component.

Once the surface of the glenoid cavity has been prepared, conventional surgical glenoid replacement processes typically require that a plurality of fixed glenoid peg accepting holes be individually drilled into the resected glenoid. To accomplish this, a drilling guide is placed on the glenoid and is used as a template to provide a path for each peripheral peg hole to be drilled. After each hole is drilled, an anti-rotation peg is inserted into that respective hole of the guide to ensure the next drilled hole is properly aligned.

Figure 6:
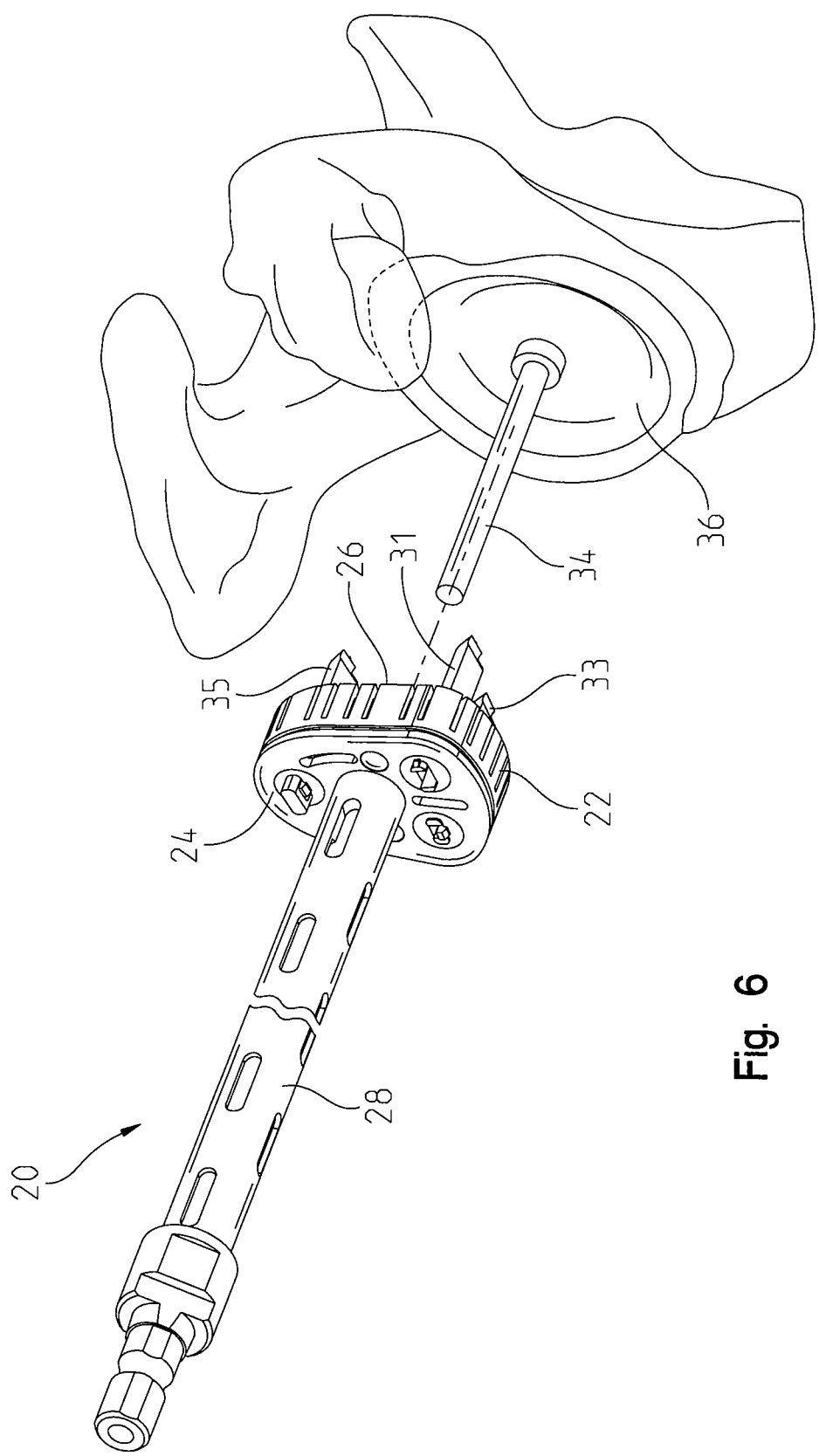
FIGS. 6-7 represent perspective views of a peripheral peg drill component in accordance with the present teachings being advanced along a guide pin prior to peripheral peg holes being drilled into a glenoid.
Figure 7:
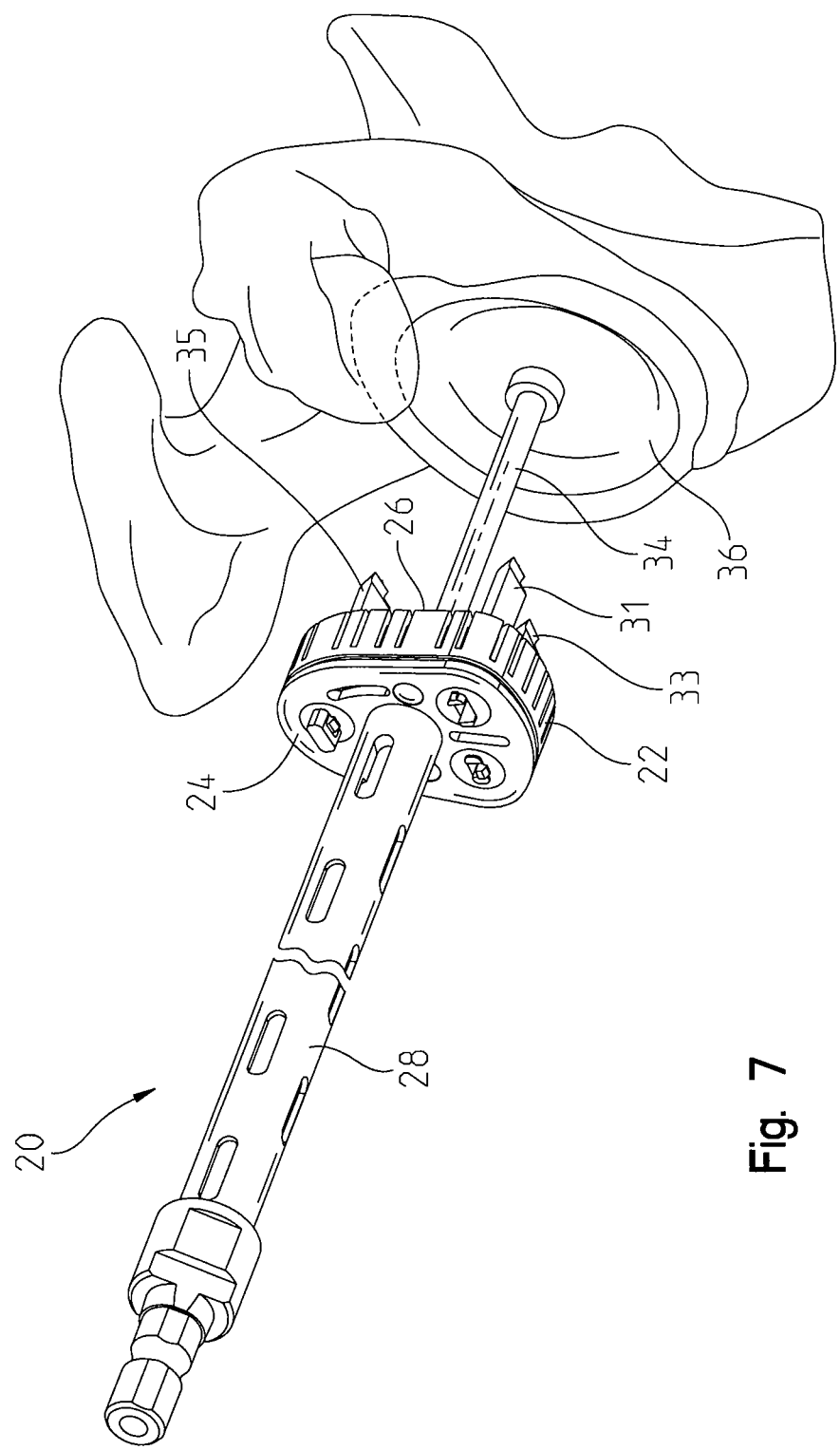
Figure 8:
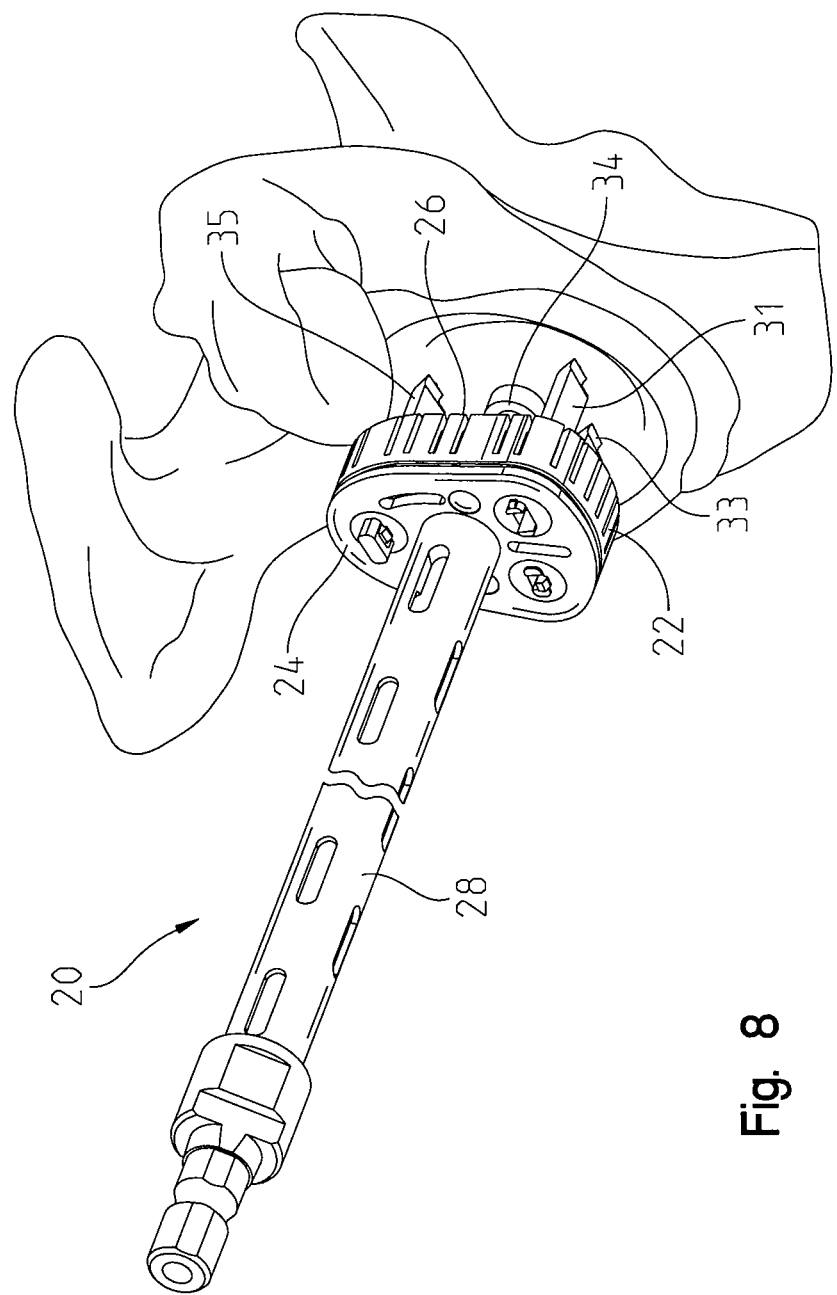
FIG. 8 represents a perspective view of a peripheral peg drill component drilling peripheral peg holes into a glenoid in accordance with the present teachings.

The present teachings, however, eliminate the need to drill each hole individually, and instead provide a means for drilling all peripheral peg holes at once. To achieve this, as shown in FIG. 5, a guide or alignment pin 34 is placed in the central guide hole 37 of the glenoid cavity 36 and is configured to penetrate the defined opening 32 positioned on of the second side 26 of the housing 22. In other words, and with reference to FIGS. 6-7, the defined opening 32 on the second side 26 of the peripheral peg drill component 20 is aligned with and advanced along the guide pin 34 until the peripheral peg drill bits 31, 33 and 35 engage the surface of the glenoid cavity 36. After the peripheral peg drill bits 31, 33 and 35 engage the glenoid cavity 36, the drill can be activated, thereby allowing all peripheral peg holes to be created simultaneously at once (see FIG. 8). The material from which the peripheral peg drill bits 31, 33 and 35 are made depends on the intended application of the drill bit. For orthopedic uses, however, the drill bits 31, 33 and 35 can be manufactured from any surgical quality metallic component including, but not limited to, stainless steel, titanium, aluminum, brass, cobalt chrome molybdenum alloys, nitinol alloys and the like. It should also be understood and appreciated herein that the size, orientation and number of drill bits 31, 33 and 35 (and/or their respective flutes) can be adjusted as necessary, particularly depending on the intended application and use of the drill bits. In accordance with one specific embodiment, the peripheral peg drill component 20 has at least two drill bits 31, 33 and 35 extending from the second side 26 of the housing 22, while in accordance with still other specific embodiments, at least three drill bits 31, 33 and 35 extend from the second side 26. As such, the present teachings are not intended to be limited herein.

Figure 9:
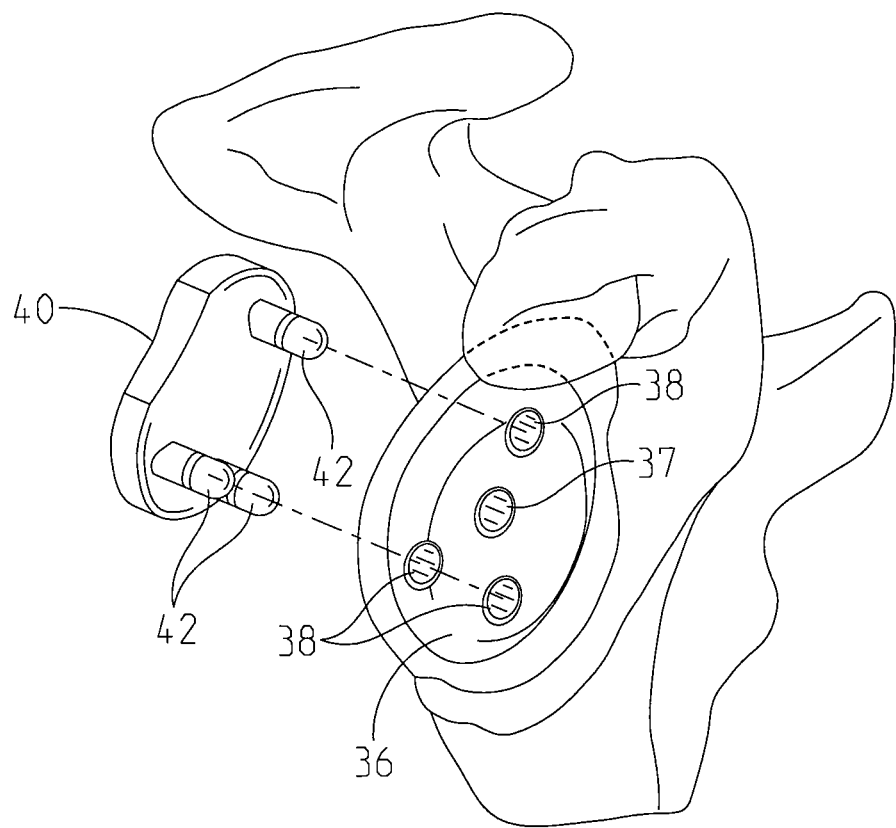
FIG. 9 represents a perspective view of a glenoid pegged component aligned for insertion into the drilled peripheral peg holes of the glenoid according to the present teachings.

As shown in FIG. 9, after the peripheral peg holes 38 are created, a glenoid component 40 can be implanted into the resected glenoid cavity 36 by aligning the peripheral pegs 42 of the glenoid component 40 with the drilled peripheral peg holes 38. It should be understood and appreciated herein that the teachings of the present application can be performed using various different geometrical peg configurations and shapes. For instance, while the present application depicts an illustrative embodiment in which the glenoid component 40 has three peripheral pegs 42, it is of course possible to perform the teachings of the present application using less or more than three peripheral pegs if desired. While not shown here, it is also envisioned that bone cement and/or various appropriate biological materials can be injected into the peripheral peg holes 38 defined within the glenoid cavity 36 before the peripheral pegs 42 of the glenoid component 40 are implanted to facilitate bonding of the component to the bone if desired. Those of skill in the art will understand how to incorporate such materials into the implantation system if necessary; therefore, a detailed discussion of the bonding process is not discussed in detail herein.

Figure 10:
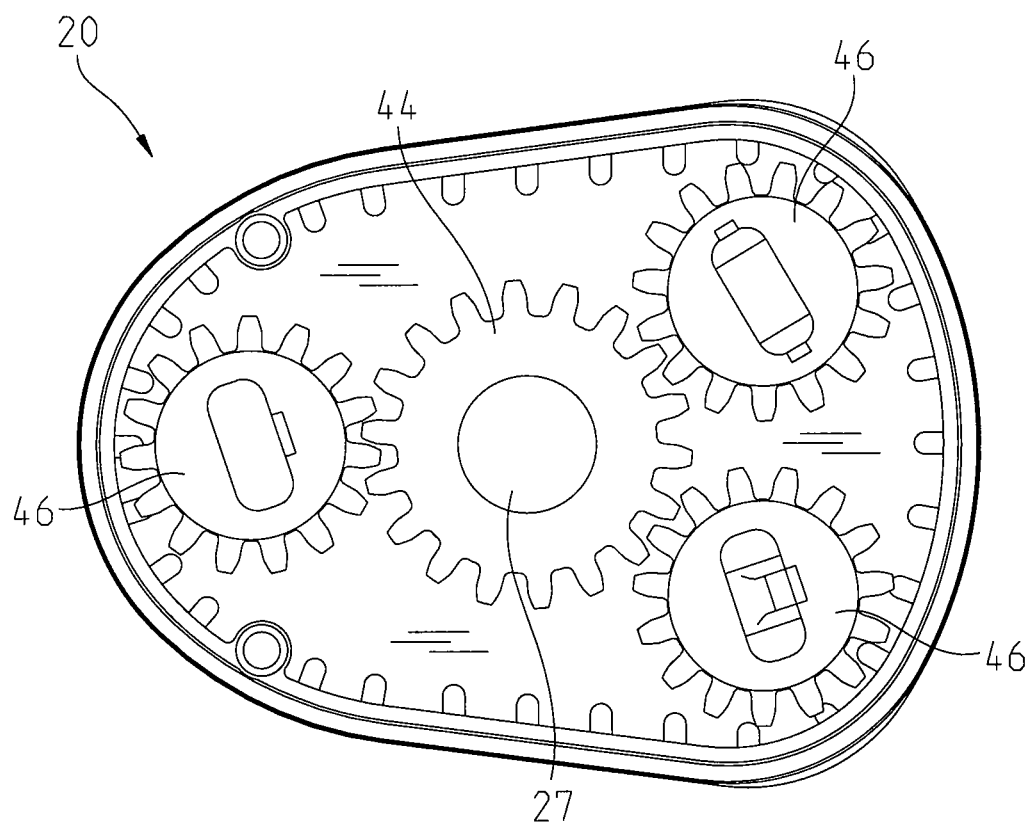
FIG. 10 represents a top view of a peripheral peg drill component having its top cover removed to reveal a spur gear system for driving the peripheral peg drill component according to the present teachings.
Figure 11:
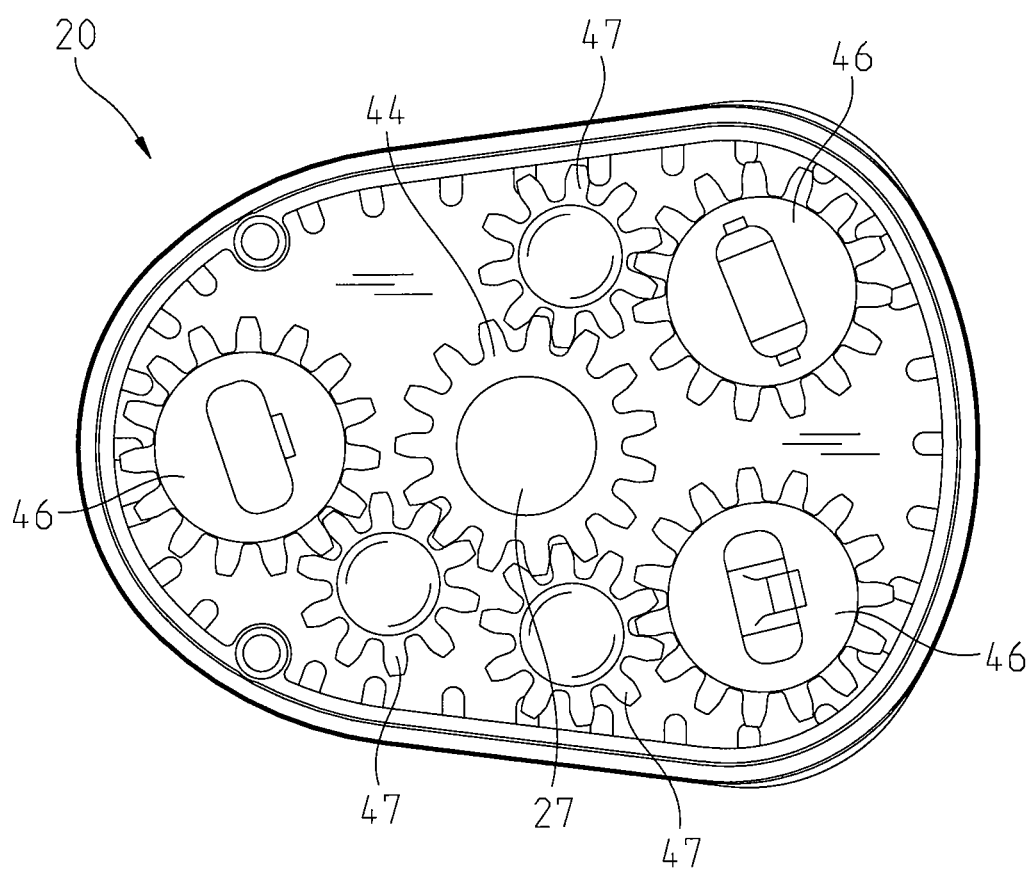
FIG. 11 represents a top view of a peripheral peg drill component having its top cover removed to reveal another spur gear system for driving the peripheral peg drill component according to the present teachings.

It should be understood and appreciated herein that various means can be used to drive the peripheral peg drill bits 31, 33 and 35 so that the peripheral peg holes 38 are created in the glenoid cavity 36. FIGS. 10 and 11, for instance, depict two illustrative means for driving the drill bits 31, 33 and 35 of the peripheral peg drill component 20 by using spur gear systems. Additional information regarding such spur gear systems can be found within U.S. Pat. Nos. 8,795,280 and 8,795,279, the pertinent teachings of which are hereby incorporated by reference herein. Specifically, FIG. 10 illustrates a standard spur gear system. Spur gear systems are generally known in the art and include various configurations of gear wheels, each having projections (teeth) that are configured to intersect or mesh with the teeth of another gear wheel, thereby transmitting force and motion alternatively from one gear to another. As is shown in this illustrative embodiment, a drive gear 44 is connected to three driven gears 46, each of which are connected to and configured to drive one of the corresponding peg drill bits 31, 33 and 35 extending from the second side 26 of the housing 22. When a drill connected to the drive shaft 28 is activated, the drive shaft 28 will cause the drive gear 44 to rotate. Because the three driven gears 46 have teeth meshing with the teeth of the drive gear 44, the driven gears 46 will be caused to rotate in the opposite direction of the drive gear 44 as it rotates. Despite rotating in the opposite direction from the drive gear 44, each of the three driven gears 46 will still rotate in the same direction as one another, and in turn, will cause their corresponding peg drill bits 31, 33 and 35 of which they are individually associated to rotate in the same direction in unison as well. In accordance with certain variations of this illustrative embodiment, it is also possible to have more than one gear stacked on top of one another, such that each gear has a different diameter for mating up with a gear on each peripheral drill bit 31, 33 and 35. Such an arrangement would allow for non-symmetrical drill locations. Moreover, in accordance with certain aspects of the present invention, the internal drive mechanism can be designed in such a manner as to create counter-clockwise turning of the drill bits to accommodate left hand cutting procedures. Accordingly, the present teachings are not intended to be limited herein.

As is shown in FIG. 11, in accordance with other illustrative embodiments of the present invention, the spur gear system used for driving the drill bits 31, 33 and 35 of the peripheral peg drill component 20 can also include additional intermediary idler gears 47 positioned between each of the driven gears 46 and the drive gear 44. As those of skill in the art will understand and appreciate, the addition of idler gears 47 can be used to keep the directional rotation of the driven gears 46 and the drive gear 44 to stay the same as the drive shaft.

Figure 12:
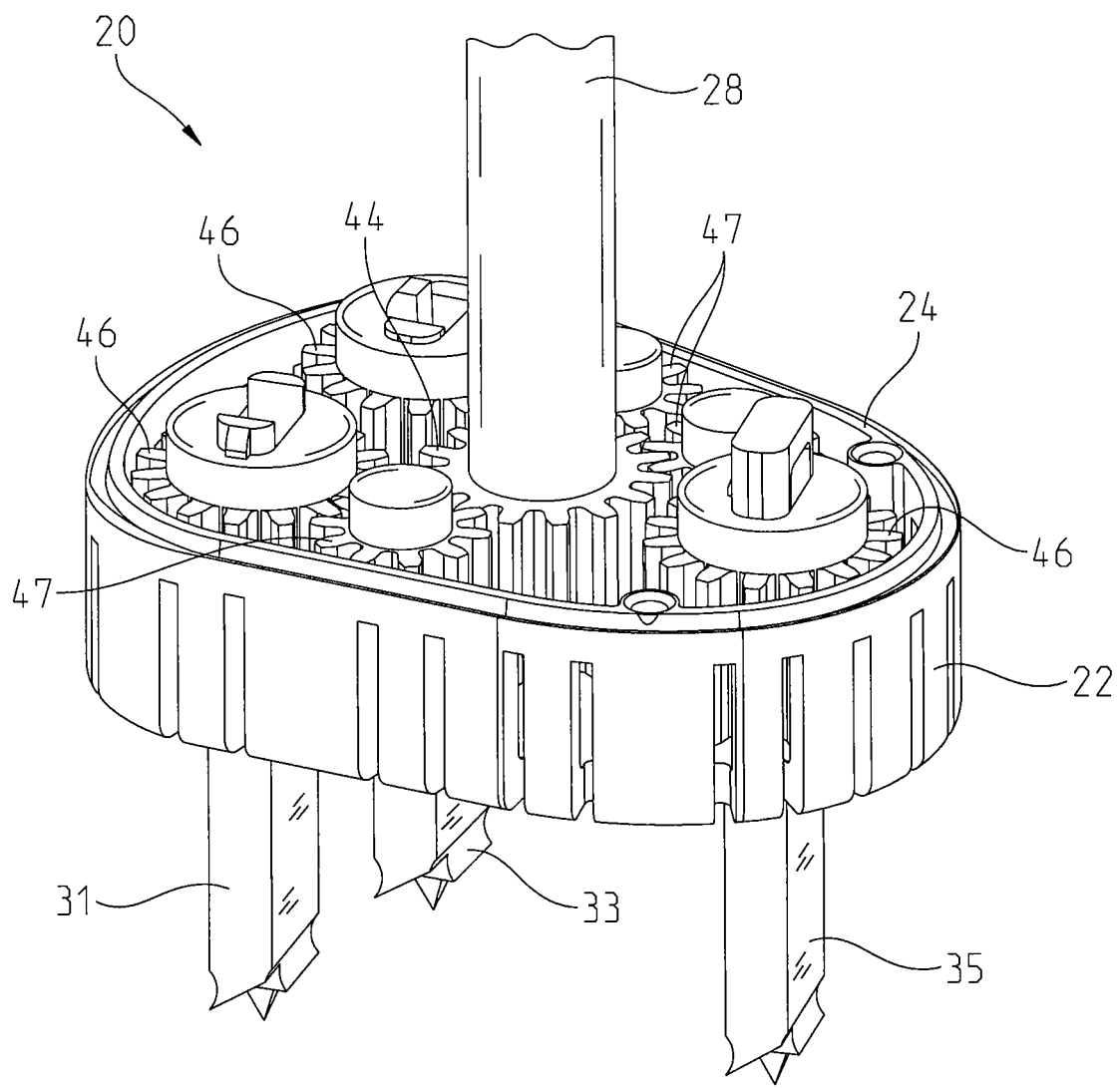
FIG. 12 represents a perspective view of a peripheral peg drill component having its top cover removed to reveal the internal gear train driving mechanism and the interchangeable drill bits in accordance with the present teachings.

Moving now to FIG. 12, a peripheral peg drill component 20 having its top cover removed to reveal the internal gear train driving mechanism and the interchangeable drill bits 31, 33 and 35 in accordance with the present teachings is shown. As will be explained in detail below, in accordance with certain embodiments herein, it may be beneficial to have the drill bits 31, 33 and 35 easily removable from the driven gears 46 within the housing 22. This removability is particularly important if the drill bits become dull or damaged, as well as when the peripheral peg drill component 20 is intended to be a reusable component. As those of skill in the relevant art will understand and appreciate herein, there are numerous ways to temporarily retain or join two components together, including, but not necessarily limited to, threaded and snap-connect fasteners.

Figure 13:
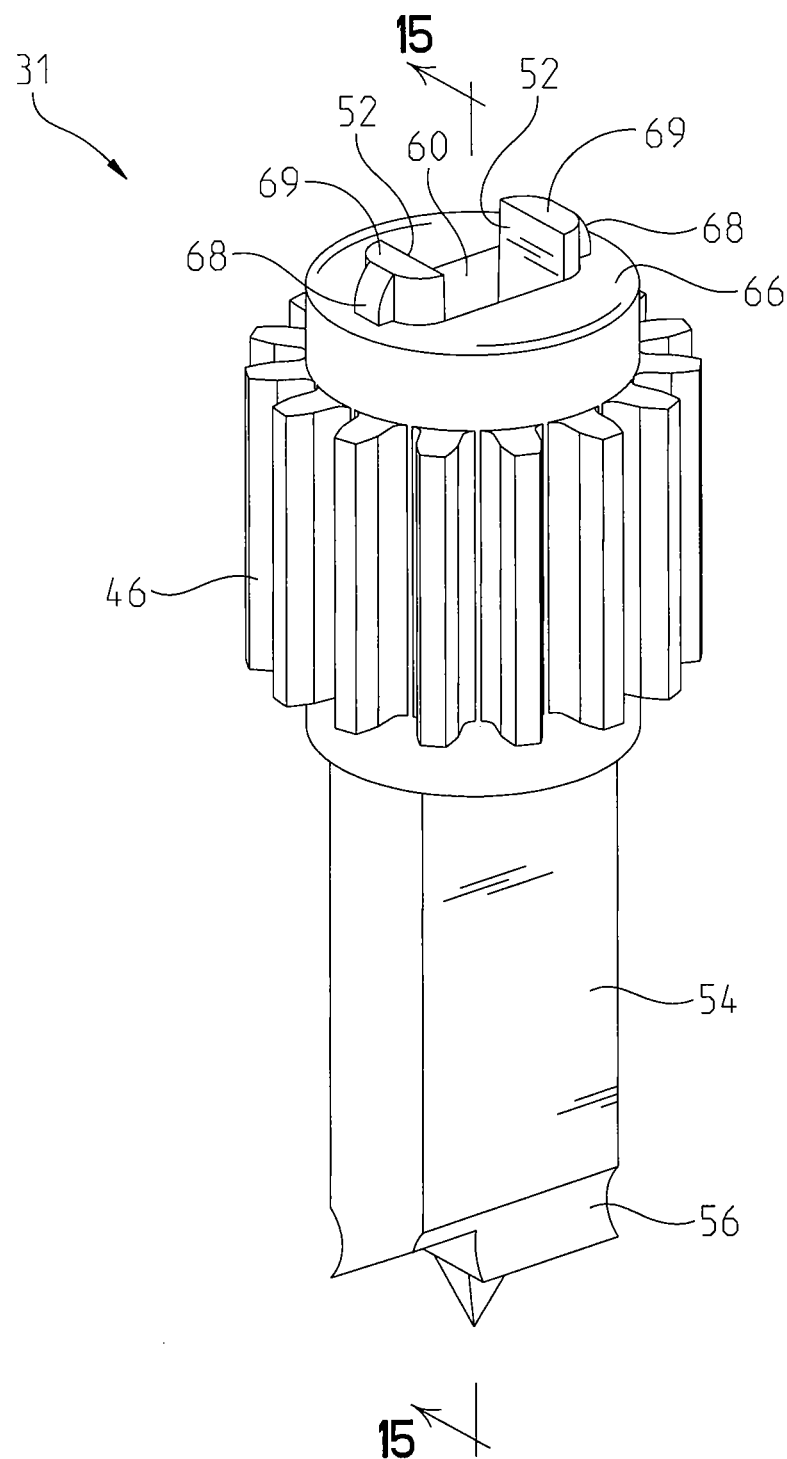
FIG. 13 represents a perspective view of a double spring finger snap drill bit associated with a gear in accordance with the present teachings.
Figure 14:
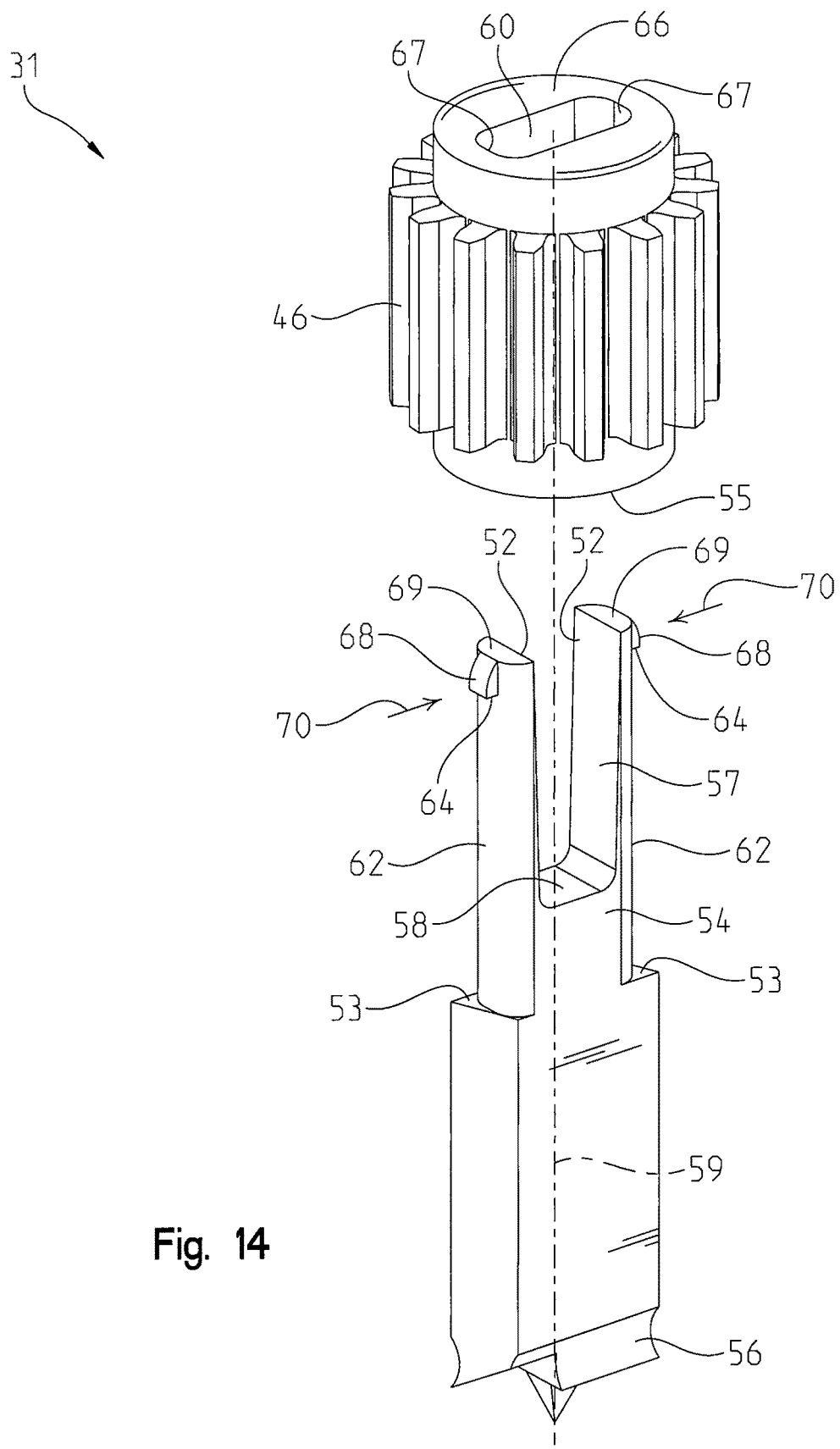
FIG. 14 represents a perspective view of the double spring finger snap drill bit of FIG. 13 exploded from the gear.
Figure 15:
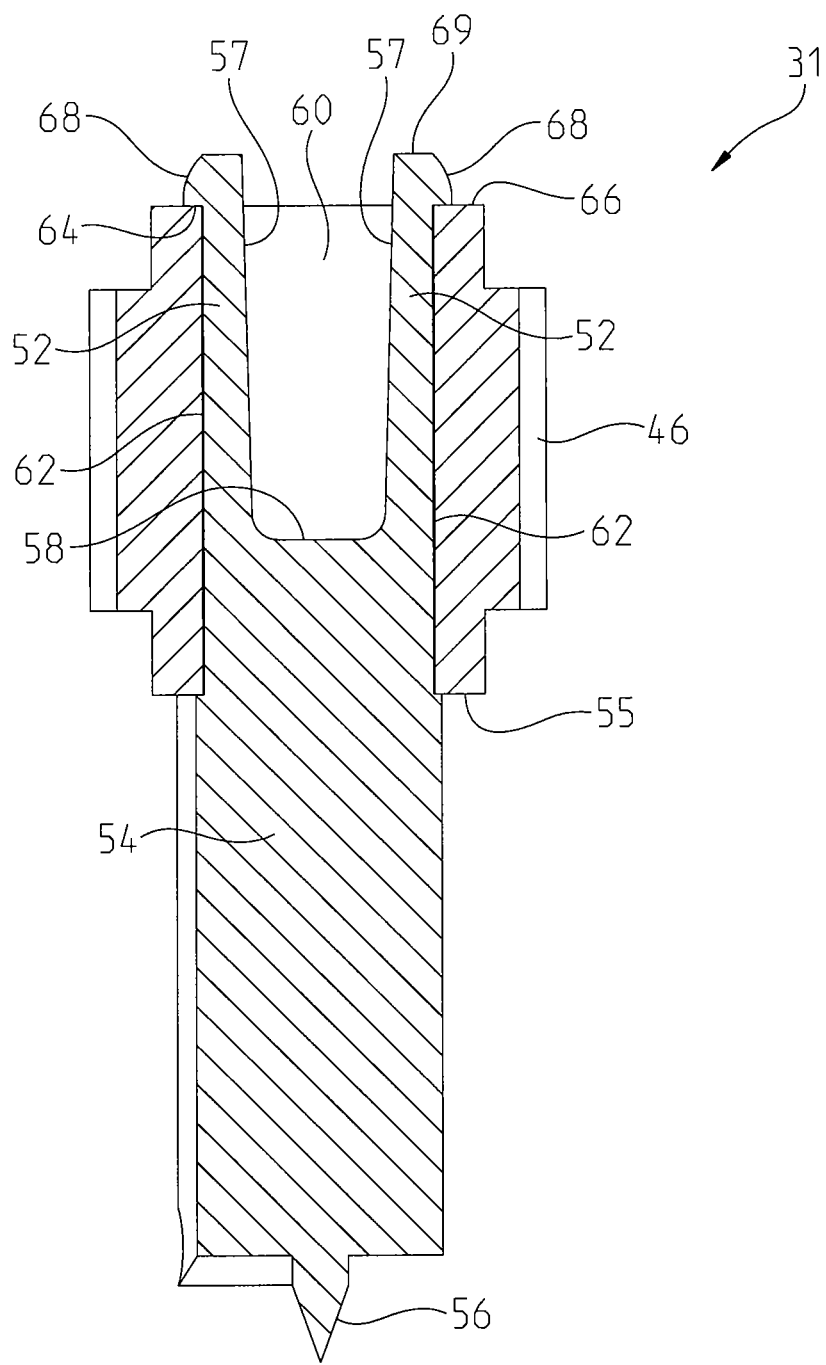
FIG. 15 represents a cross-sectional perspective view of the double spring finger snap drill bit and gear of FIG. 13.

FIGS. 13-15 depict a first illustrative double spring finger snap drill bit 31 in accordance with the present teachings. In accordance with this embodiment, the drill bit 31 includes a pair of resiliently deformable spring fingers or tines 52 that extend from a drill body 54. The drill body 54 is composed of a drill spade 56 on one end for engaging the bone during a surgical procedure and a shoulder 58 on its opposite end. Those of skill in the art will understand herein that any type of drill spade or cutting shape can be used in accordance with the present teachings. As such, the present disclosure is not intended to be limited herein. In accordance with this embodiment, the tines 52 extend from the shoulder 58 in a U-shaped manner. When the drill bit 31 is installed onto the drill component 20, the tines 52 are advanced through an oblong shaped channel 60 that passes entirely through one of the driven gears 46 along a longitudinal axis 59 until a locking engagement is achieved. To achieve this locking engagement, each tine has a tab 68 which extends beyond an outer surface 62 and is configured to press against the sidewalls 67 of the channel 60 during insertion so that the tines are each caused to deflect inwardly as they are advanced through the gear 46. Each tab 68 further includes an abutment platform 64 such that when the end 69 of each tine 52 exits the channel 60, the tines spring outwardly to recover their pre-deflected configuration, thereby causing the abutment platforms 64 to achieve a snap-fit engagement with the top surface 66 of the gear 46 (i.e., the faces of the abutment platforms 64 engage the top surface 66 of the gear). In addition, as the abutment platforms 64 engage the top surface 66, the outer surfaces 62 of the tines 52 also engage the respective sidewalls 67, thereby preventing the tines 52 from being pulled back out through the channel 60. At the base of each of the pair of tines 52 is also a stop surface 53, each of which are configured to engage the bottom surface 55 of the gear 46 as the tines are advanced through the channel 60. As those of skill in the art will understand and appreciate herein, these stop surface 53 are designed to prevent the tines 52 from being advanced into the channel 60 beyond a predetermined point and so that the drill spade 56 is able to securely engage the bone's surface without the drill bit 31 dislodging during the cutting operation.

To remove the drill bit 31 from the gear 46, pressure can be inwardly exerted on the pair of tabs 68 in the direction indicated by the arrows 70. By moving the tines 52 inward (i.e., such that the back surfaces 57 of the tines extends beyond the longitudinal axis 59 of the channel), the abutment platforms 64 disengage from the top surface 66 of the gear 46, thereby breaking the compressive clamping-force exerted between the top surface 66 and the abutment platforms 64 and the outer surfaces 62 and the sidewalls 67. Once these engagement surfaces are disengaged, the tines 52 are then capable of being retracted from the channel 60, and then the drill bit 31 removed from the gear 46.

Figure 16:
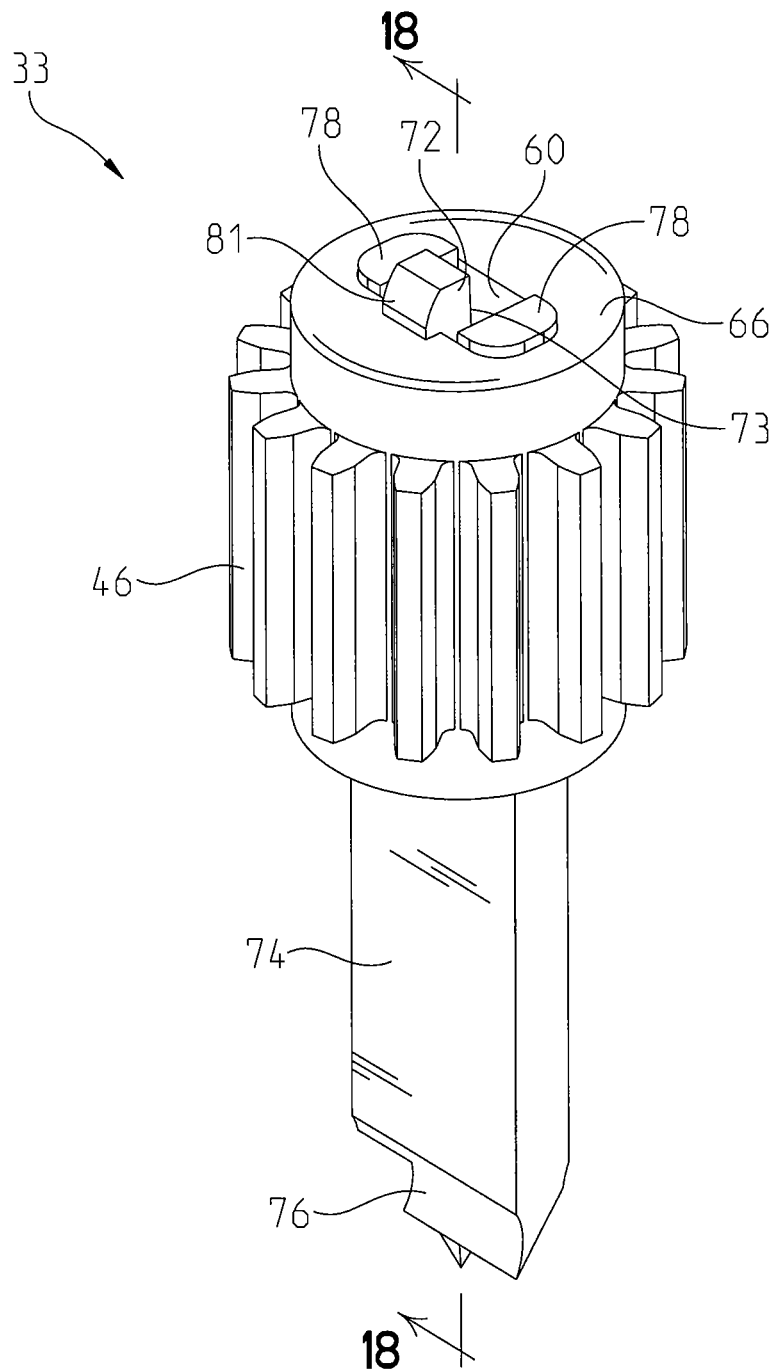
FIG. 16 represents a perspective view of a single spring finger snap drill bit associated with a gear in accordance with the present teachings.
Figure 17:
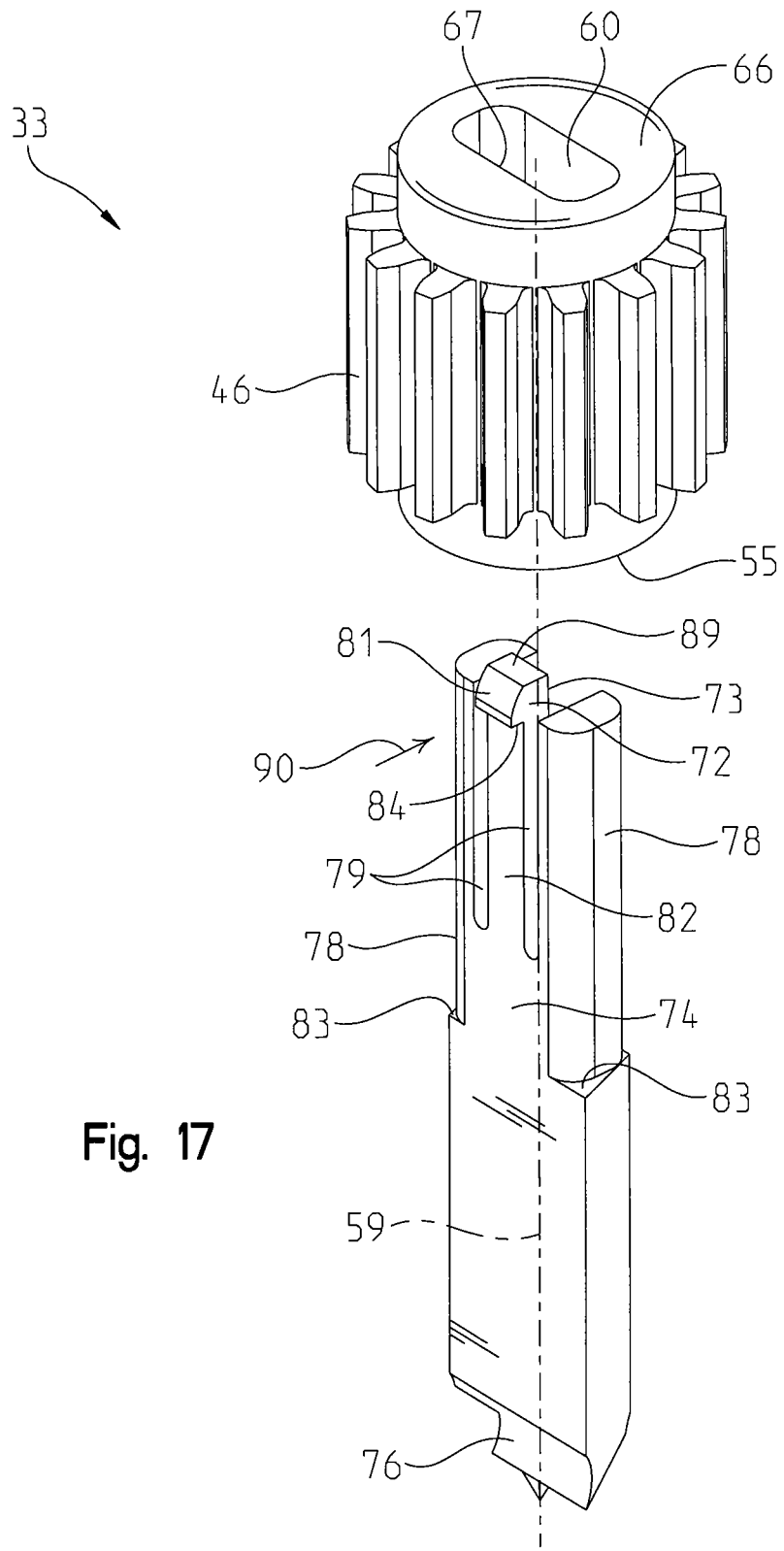
FIG. 17 represents a perspective view of the single spring finger snap drill bit of FIG. 16 exploded from the gear.
Figure 18:
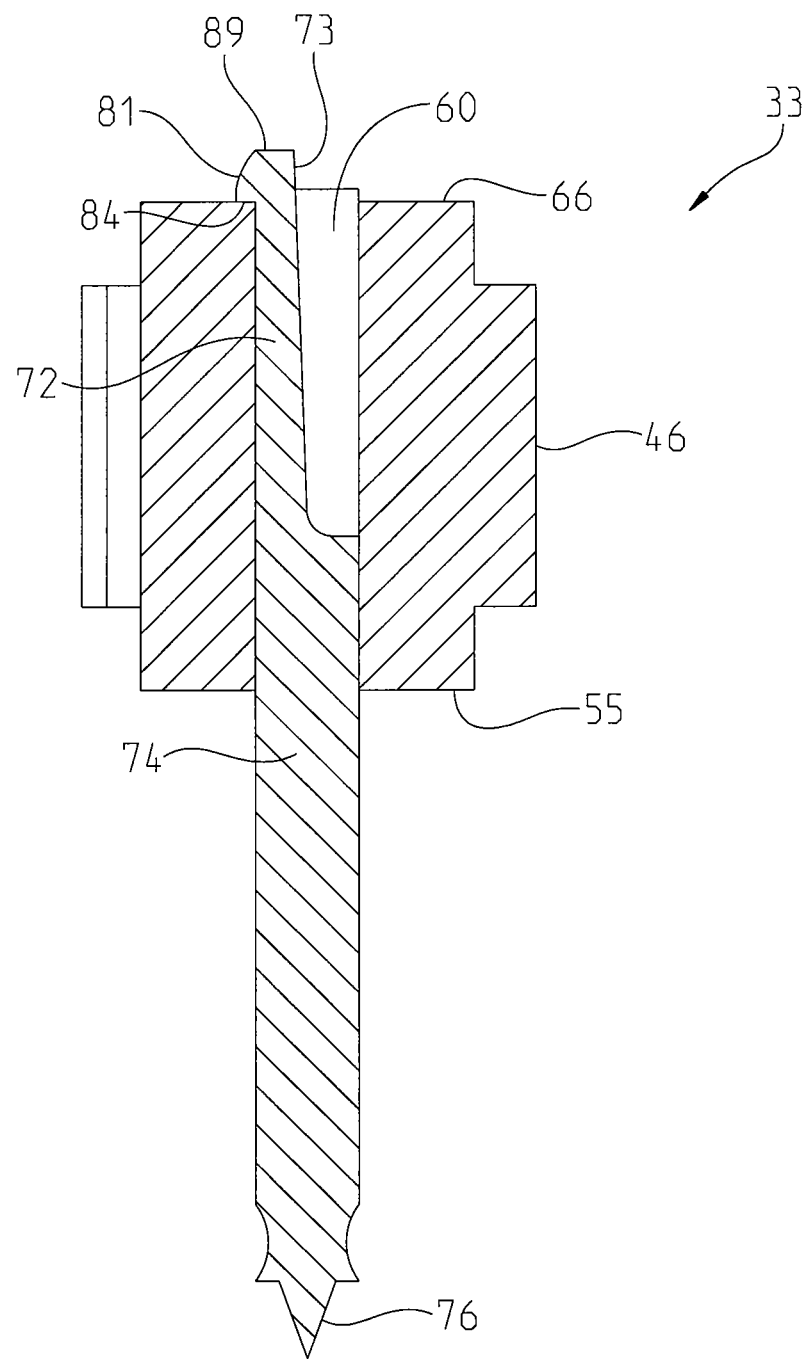
FIG. 18 represents a cross-sectional perspective view of the single spring finger snap drill bit and gear of FIG. 16.

FIGS. 16-18 depict a single spring finger snap drill bit 33 in accordance with the present teachings. In accordance with this embodiment, the drill bit 33 includes a single resiliently deformable spring finger or tine 72 that extends from a drill body 74. The drill body 74 is composed of a drill spade 76 on one end for engaging the bone during a surgical procedure and a pair of tangs 78 on its opposite end for advancing the drill bit 33 into the gear 46. In accordance with this embodiment, the tine 72 is positioned between the pair of tangs 78 such that a small void 79 is created on each side of the tine. When the drill bit 33 is installed onto the drill component 20, the tine 72 and tangs 78 are advanced through an oblong channel 60 that passes entirely through one of the driven gears 46 along a longitudinal axis 59 until a snapping engagement is achieved. To achieve this locking engagement, the tine 72 includes a tab 81 which extends beyond an outer surface 82 and is configured to press against a sidewall 67 of the channel 60 during insertion so that the tine 72 is caused to deflect inwardly as it is advanced through the gear 46. The tab 81 further includes an abutment platform 84 such that when the end 89 of the tine 72 exits the channel 60, the tine 72 springs outwardly to recover its pre-deflected configuration, thereby causing the abutment platform 84 to achieve a snap-fit engagement with the top surface 66 of the gear 46 (i.e., the face of the abutment platform 84 engages the top surface 66 of the gear). In addition, as the abutment platform 84 engages the top surface 66, the outer surface 82 of the tine 72 also engages the sidewall 67, thereby preventing the tine 72 from being pulled back out through the channel 60. At the base of each of the pair of tangs 78 is also a stop surface 83, each of which are configured to engage the bottom surface 55 of the gear 46 as the tangs 78 are advanced through the channel 60. As those of skill in the art will understand and appreciate herein, these stop surface 83 are designed to prevent the tine 72 from being advanced into the channel 60 beyond a predetermined point and so that the drill spade 76 is able to securely engage the bone's surface without the drill bit 33 dislodging during the cutting operation.

To remove the drill bit 33 from the gear 46, pressure can be inwardly exerted on the tab 81 of the tine 72 in the direction indicated by the arrow 90. By moving the tine 72 inward (i.e., such that a back surface 73 of the tine extends beyond the longitudinal axis 59 of the channel), the abutment platform 84 disengages from the top surface 66 of the gear 46, thereby breaking the compressive clamping-force exerted between the top surface 66 and the abutment platform 84 and the outer surface 82 and the sidewall 67. Once these engagement surfaces are disengaged, the tine 72 is then capable of being retracted from the channel 60, and thereby ultimately releasing the drill bit 33 from the gear 46.

Figure 19:
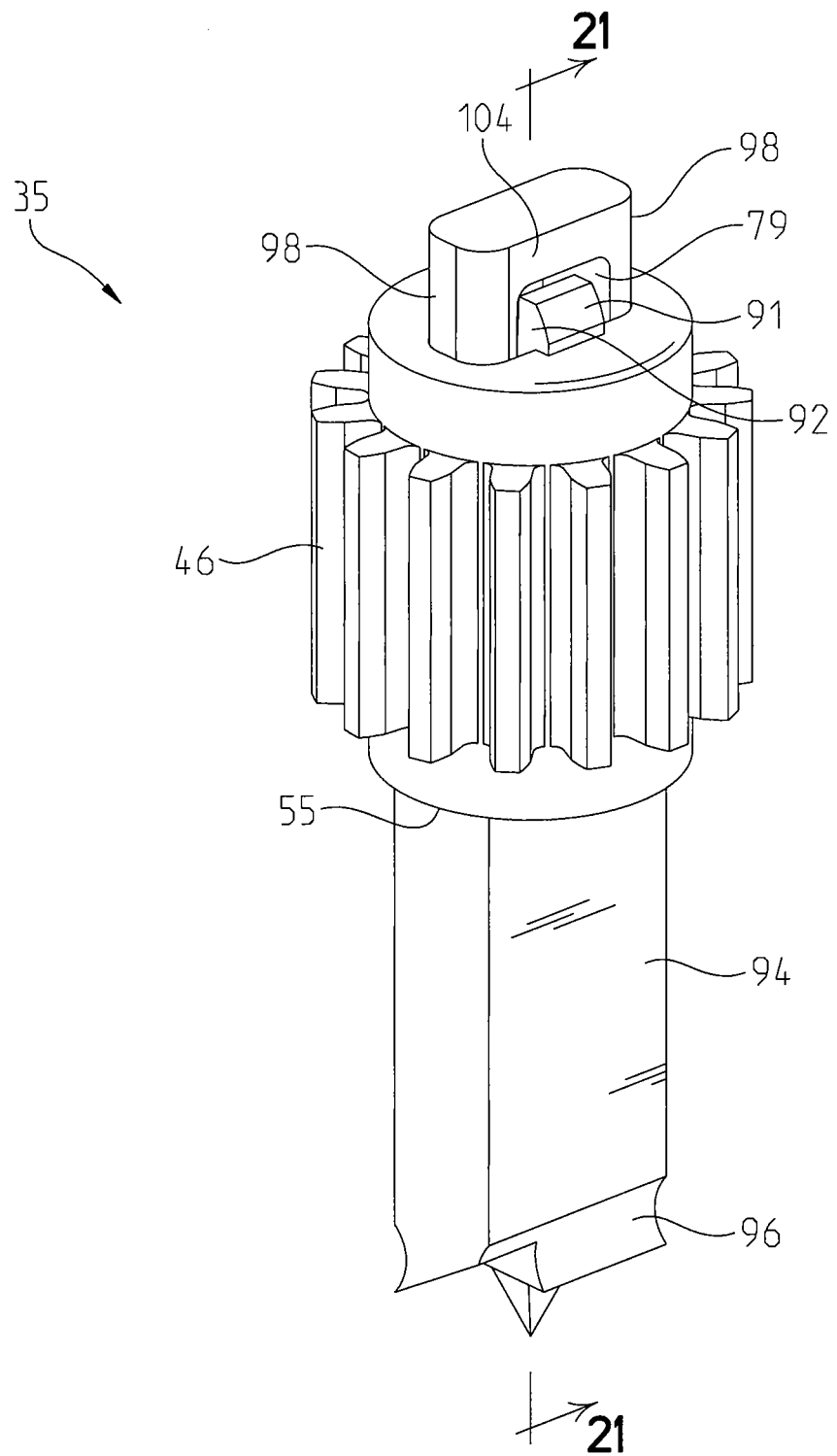
FIG. 19 represents a perspective view of another single spring finger snap drill bit associated with a gear in accordance with the present teachings.
Figure 20:
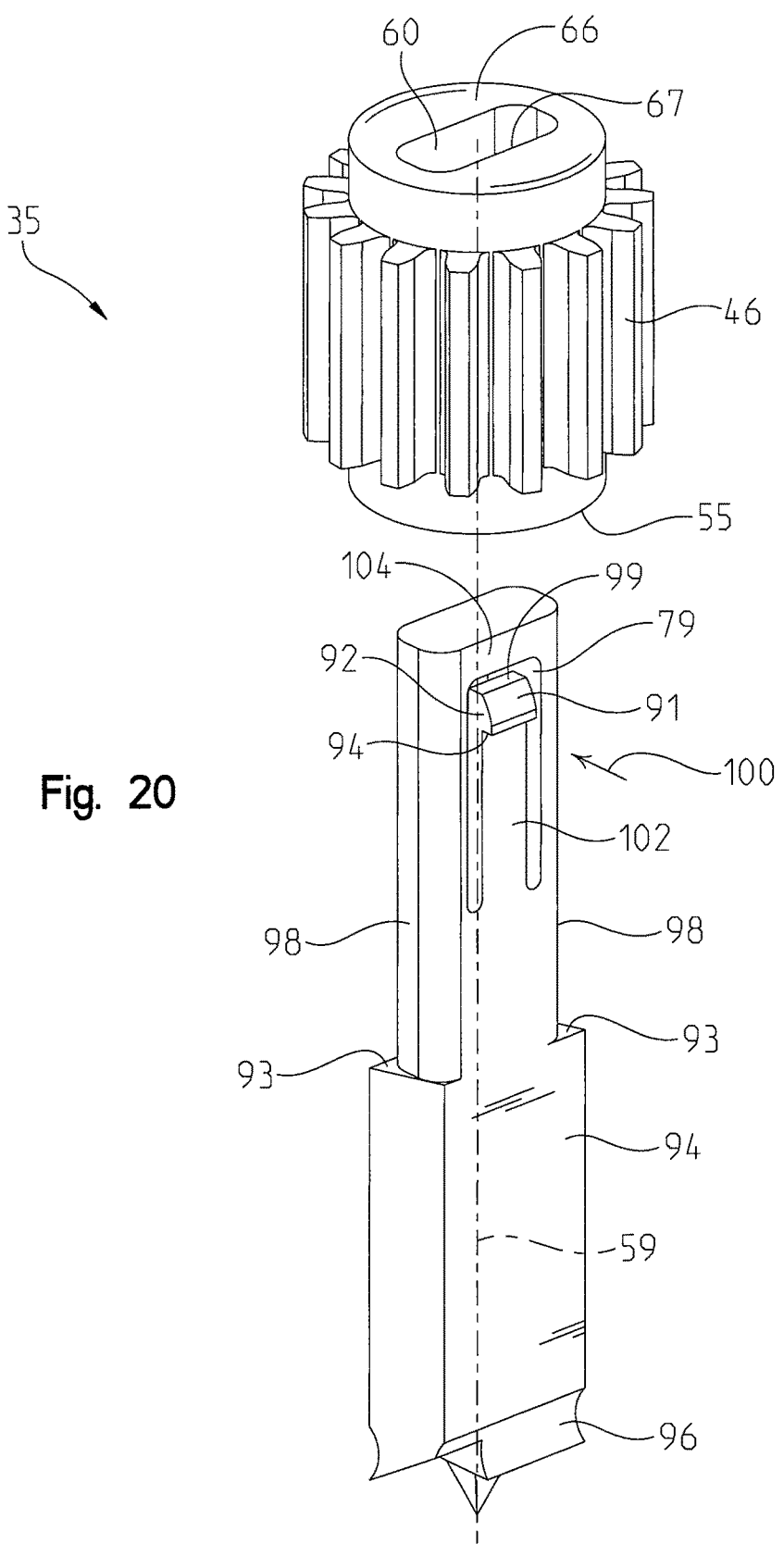
FIG. 20 represents a perspective view of the single spring finger snap drill bit of FIG. 19 exploded from the gear.
Figure 21:
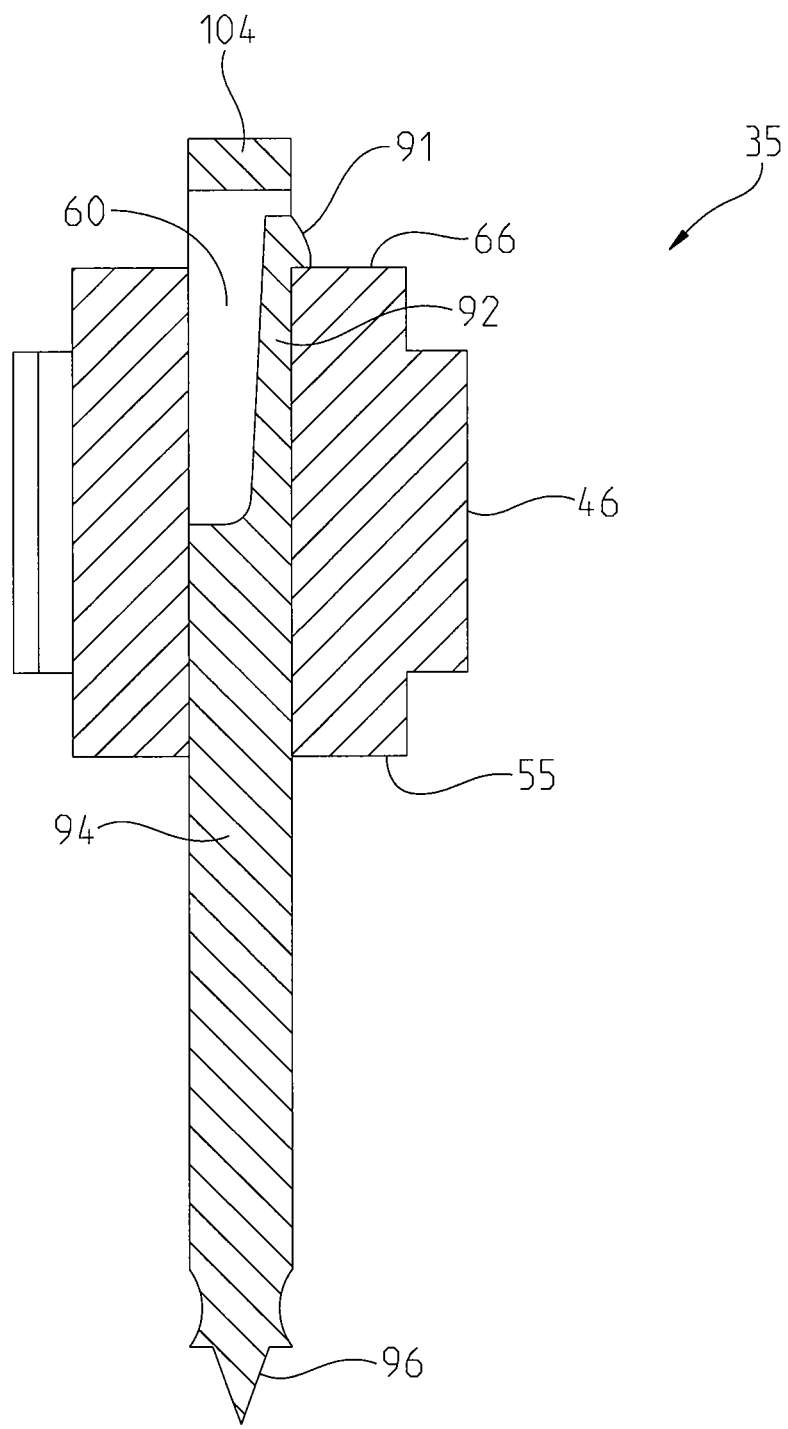
FIG. 21 represents a cross-sectional perspective view of the single spring finger snap drill bit and gear of FIG. 19.

FIGS. 19-21 depict another single spring finger snap drill bit 35 in accordance with the present teachings. In accordance with this embodiment, the drill bit 35 includes a single resiliently deformable spring finger or tine 92 that extends from a drill body 94. The drill body 94 is composed of a drill spade 96 on one end for engaging the bone during a surgical procedure and a pair of tangs 98 on its opposite end for advancing the drill bit 35 into the gear 46. In accordance with this embodiment, the tine 92 is positioned between are partially encased by the pair of tangs 98 such that a small void 79 is created on each side of the tine, as well its top surface. When the drill bit 35 is installed onto the drill component 20, the tine 92 and tangs 98 are advanced through an oblong channel 60 that passes entirely through one of the driven gears 46 along a longitudinal axis 59 until a snapping engagement is achieved. To achieve this locking engagement, the tine 92 includes a tab 91 which extends beyond an outer surface 102 and is configured to press against a sidewall 67 of the channel 60 during insertion so that the tine 92 is caused to deflect inwardly as it is advanced through the gear 46. The tab 91 further includes an abutment platform 94 such that when the end 99 of the tine 92 exits the channel 60, the tine 92 springs outwardly to recover its pre-deflected configuration, thereby causing the abutment platform 94 to achieve a snap-fit engagement with the top surface 66 of the gear 46 (i.e., the face of the abutment platform 94 engages the top surface 66 of the gear). In addition, as the abutment platform 94 engages the top surface 66, the outer surface 102 of the tine 92 also engage the sidewall 67, thereby preventing the tine 92 from being pulled back out through the channel 60. At the base of each of the pair of tangs 98 is also a stop surface 93, each of which are configured to engage the bottom surface 55 of the gear 46 as the tangs 98 are advanced through the channel 60. As those of skill in the art will understand and appreciate herein, these stop surfaces 93 are designed to prevent the tine 92 from being advanced into the channel 60 beyond a predetermined point and so that the drill spade 96 is able to securely engage the bone's surface without dislodging the drill bit 35 during the cutting operation.

Unlike the embodiment shown in FIGS. 16-18, the tangs 98 of this illustrative embodiment are connected by a bridge 104 at one end. As those of skill in the art will understand and appreciate herein, by having a bridge 104 spanning across the tangs, the structural integrity of the drill bit 35 is reinforced and strengthened during operation.

To remove the drill bit 35 from the gear 46, pressure can be inwardly exerted on the tab 91 on the tine 92 in the direction indicated by the arrow 100. By moving the tine 92 inward (i.e., such that a back surface of the tine extends beyond the longitudinal axis 59 of the channel), the abutment platform 94 disengages from the top surface 66 of the gear 46, thereby breaking the compressive clamping-force exerted between the top surface 66 and the abutment platform 94 and the outer surface 102 and the sidewall 67. Once these engagement surfaces are disengaged, the tine 92 is then capable of being retracted from the channel 60, and thereby ultimately releasing the drill bit 35 from the gear 46.

While an exemplary embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

The terminology used herein is for the purpose of describing particular illustrative embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations).

What is claimed is:

1. A drill bit, comprising:
a cutting portion having an edge for penetrating bone;
a resilient tine configured to be inserted into a drill housing, the resilient tine including a tab having an abutment surface, the abutment surface configured to establish a snap-fit connection with a drill gear within the drill housing, the abutment surface being disengageable from the drill gear to remove the drill bit from the drill housing;
a first tang parallel to the resilient tine, the first tang positioned such that the resilient tine moves out of parallel alignment during insertion or removal of the drill bit; and
a pair of tangs at least partially encasing the resilient tine, the pair of tangs including the first tang;
wherein the pair of tangs is connected by a strengthening bridge.

2. A drill bit, comprising:
a cutting portion having an edge for penetrating bone;
a shank portion configured to be inserted into a drill housing, the shank portion including a resilient tine that is movable from a first position to a second position;
a tab extending from the resilient tine, the tab including an abutment surface that is configured to snappingly engage a surface of a drill gear;
a first tang parallel to the resilient tine, the first tang positioned such that the resilient tine moves out of parallel alignment during insertion or removal of the drill bit; and
a pair of tangs at least partially encasing the resilient tine, the pair of tangs including the first tang;
wherein the pair of tangs is connected by a strengthening bridge.

3. A drill assembly, comprising:
a housing having a first side and a second side opposite the first side;
a drill bit having a cutting edge for penetrating bone and a resilient tine configured to be inserted into the housing; and
a driving mechanism having a drill gear configured to rotate the drill bit and penetrate the bone, the drill gear including a channel for receiving the resilient tine;
wherein the resilient tine includes a tab having an abutment surface configured to establish a snap-fit connection with a drill gear.

4. The drill assembly of claim 3, wherein the drill bit further comprises a second resilient tine configured to establish a snap-fit connection with the drill gear.

5. The drill assembly of claim 4, wherein the second resilient tine is substantially parallel to the resilient tine.

6. The drill bit assembly of claim 3, wherein the drill bit further comprises a stop surface configured to engage a surface of the drill gear as the drill bit is inserted through the channel of the drill gear.

7. The drill bit assembly of claim 6, wherein the stop surface is substantially parallel to the abutment surface of the tab.

8. The drill bit assembly of claim 3, wherein the drill bit further comprises a pair of tangs at least partially encasing the resilient tine.

9. The drill bit assembly of claim 8, wherein the drill bit further comprises a channel separating the resilient tine from the pair of tangs.

10. The drill bit assembly of claim 8, wherein the pair of tangs is connected by a strengthening bridge.

* * * * *